US009162937B2

(12) United States Patent
Grasso et al.

(10) Patent No.: US 9,162,937 B2
(45) Date of Patent: Oct. 20, 2015

(54) PROCESS TO MAKE OLEFINS FROM ORGANICS WITH REDUCED SIDE REACTIONS

(75) Inventors: Giacomo Grasso, Brussels (BE); Nikolai Nesterenko, Nivelles (BE); Sander Van Donk, Sainte-Adresse (FR); Jean-Pierre Dath, Beloeil (BE); Eric Duchesne, Waterloo (BE)

(73) Assignee: TOTAL RESEARCH & TECHNOLOGY FELUY, Seneffe (Feluy) (BE)

( * ) Notice: Subject to any disclaimer, the term of this patent is extended or adjusted under 35 U.S.C. 154(b) by 804 days.

(21) Appl. No.: 13/055,019

(22) PCT Filed: Jul. 3, 2009

(86) PCT No.: PCT/EP2009/058439
§ 371 (c)(1),
(2), (4) Date: Apr. 19, 2011

(87) PCT Pub. No.: WO2010/012564
PCT Pub. Date: Feb. 4, 2010

(65) Prior Publication Data
US 2011/0190563 A1 Aug. 4, 2011

(30) Foreign Application Priority Data
Jul. 29, 2008 (EP) ..................................... 08161378

(51) Int. Cl.
*C07C 1/20* (2006.01)

(52) U.S. Cl.
CPC ........................................ *C07C 1/20* (2013.01)

(58) Field of Classification Search
USPC ................................................. 585/648–642
See application file for complete search history.

(56) References Cited

U.S. PATENT DOCUMENTS

| | | | |
|---|---|---|---|
| 2,709,195 A * | 5/1955 | Hines ............................ | 585/638 |
| 4,311,865 A * | 1/1982 | Chen et al. .................... | 585/640 |
| 4,542,252 A * | 9/1985 | Graziani et al. .............. | 585/640 |
| 4,555,495 A * | 11/1985 | Krishnamurthy ................ | 502/50 |
| 2004/0152935 A1* | 8/2004 | Jones et al. .................... | 585/530 |
| 2004/0254413 A1* | 12/2004 | Martens et al. ............... | 585/639 |
| 2006/0149106 A1 | 7/2006 | Xiao et al. | |
| 2007/0203383 A1* | 8/2007 | Bozzano et al. .............. | 585/639 |

FOREIGN PATENT DOCUMENTS

| | | |
|---|---|---|
| CN | 1352627 A | 6/2002 |
| CN | 1688523 A | 10/2005 |
| JP | 01090136 A * | 9/1987 |
| WO | 2007/102916 A2 | 9/2007 |

OTHER PUBLICATIONS

Office Action issued in Chinese Application No. 20098128886.5 dated Nov. 5, 2012, and English translation thereof (14 pages).
Office Action and Search Report issued in Chinese Application No. 20098128886.5 dated Jul. 23, 2013, and English translation thereof (15 pages).

* cited by examiner

*Primary Examiner* — In Suk Bullock
*Assistant Examiner* — Sharon Pregler

(57) ABSTRACT

The present invention is a process for making an olefin product from an oxygen-containing organic feedstock comprising:
providing a mixture of said oxygen-containing feedstock, an hydrocarbon and optionally an inert diluent,
contacting said mixture in a reaction zone having an inner surface (the MTO reactor) with a zeolitic catalyst at conditions effective to convert at least a part of the oxygen-containing organic feedstock to olefin products (the MTO reactor effluent),
recovering a reactor effluent comprising light olefins, a heavy hydrocarbon fraction and undesired by-products, wherein:
at least a part of the inner surface is passivated such that the undesired by-products are reduced by comparison with a non passivated inner surface and/or
one or more sulphur compound is co-injected with the said oxygen-containing feedstock and the hydrocarbon and said sulphur compound is capable to reduce the undesired by-products by comparison with a non injection of sulphur compound.
The present invention is of high interest for the catalyst of the ZSM type such as ZSM-5 optionally containing phosphorus and regenerated in the MTO reactor.

19 Claims, 4 Drawing Sheets

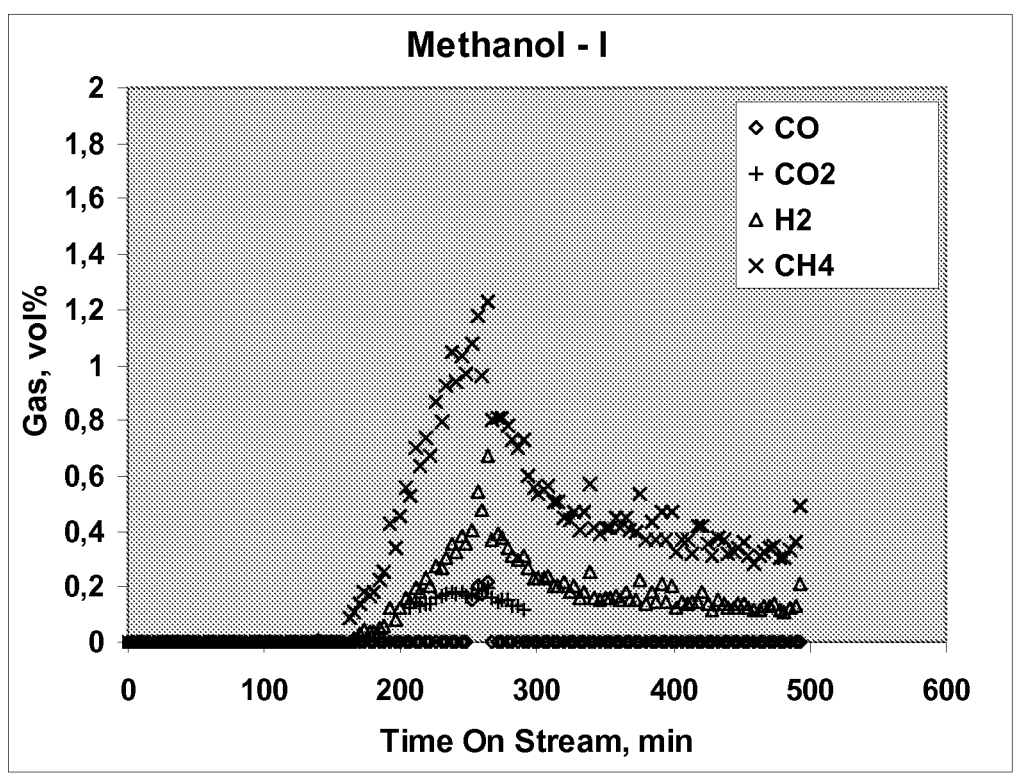
Fig 1 (comparative I)

Fig 2 (comparative II)
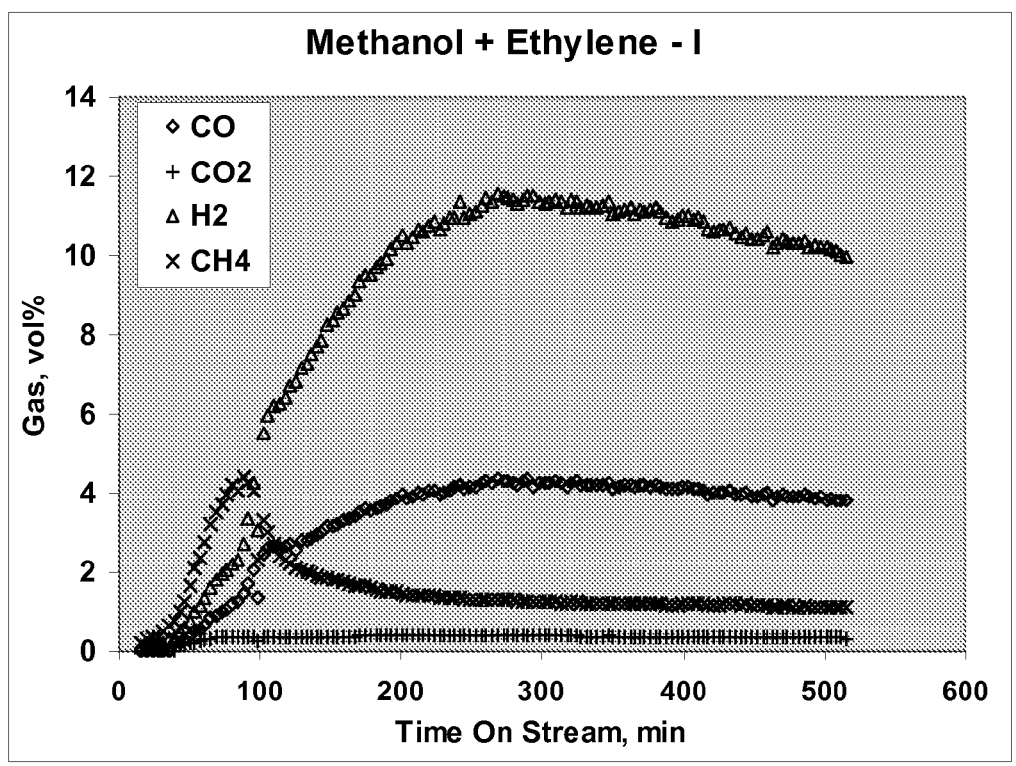

Fig 3 (comparative III)
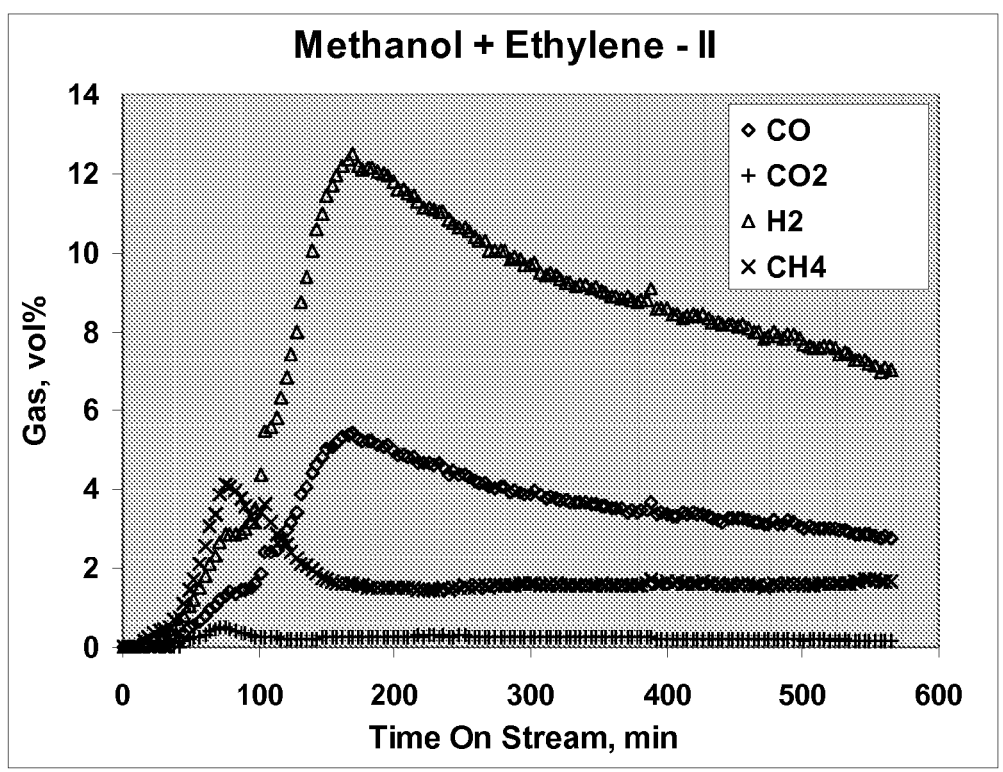

Fig 4 (according to invention)
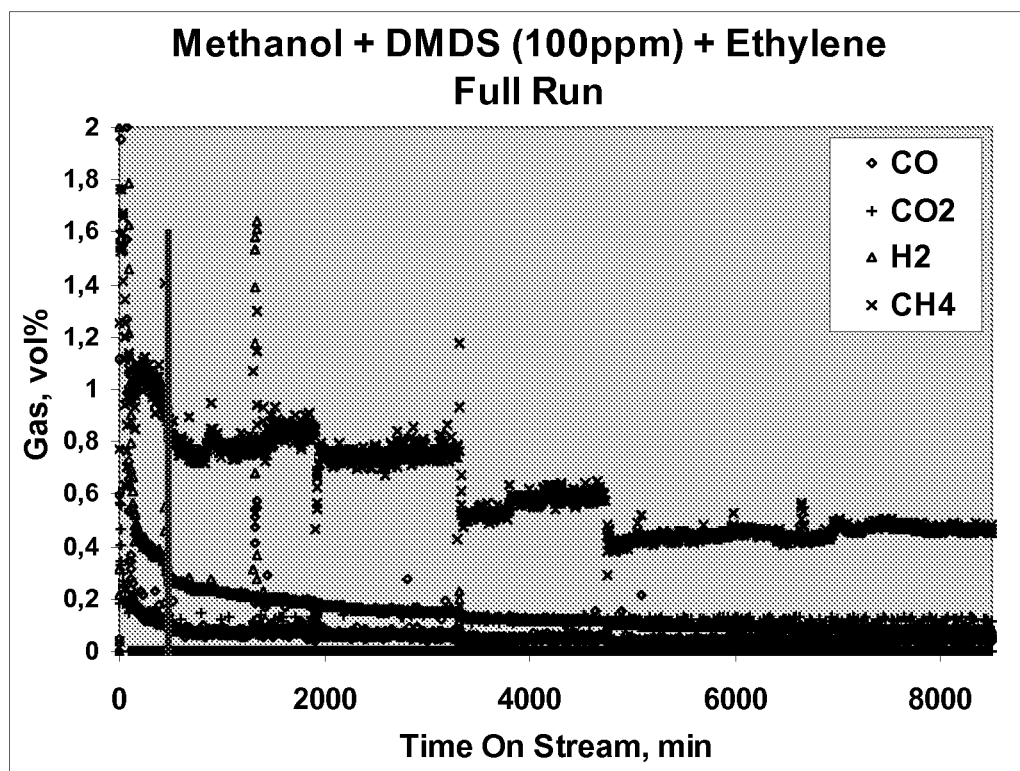

PROCESS TO MAKE OLEFINS FROM ORGANICS WITH REDUCED SIDE REACTIONS

CROSS-REFERENCE TO RELATED APPLICATIONS

This application claims the benefit of PCT/EP2009/058439, filed Jul. 3, 2009, which claims priority from EP 08161378.8, filed Jul. 29, 2008.

FIELD OF THE INVENTION

The present invention relates to a process to make olefins from organics with reduced side reactions. The limited supply and increasing cost of crude oil has prompted the search for alternative processes for producing hydrocarbon products. One such process is the conversion of oxygen-containing (by way of example methanol) to hydrocarbons and especially light olefins (by light olefins is meant $C_2$ to $C_4$ olefins) or gasoline and aromatics. In the present application the conversion of said oxygen-containing (also referred as oxygenates) is referred as MTO process. The interest in the MTO process is based on the fact that feedstocks, especially methanol can be obtained from coal, hydrocarbon residu's, biomass, organic waste or natural gas by the production of synthesis gas which is then processed to produce methanol.

The present invention discloses a process for producing light olefins (mainly propylene) with reduced metal catalyzed side-reaction by-products formation from the feed containing oxygenates and hydrocarbon and optionally any inert diluent (steam, nitrogen etc) wherein internal metal surface is protected from coking by protective layer. The passivation of the metal surface can be performed by employing either the protecting layer or pre-treatment procedure. The pre-treatment of the reactors walls could be performed by injection of sulfur containing compounds. The protecting layer can be built either before reaction by coating the metal surface, or during the reaction in-situ by co-injecting sulfur containing compounds with the feed.

This invention can be used for any type of reactors: moving, fixed or fluidized bed but is especially useful in case if the regeneration of the catalyst is performed in the same vessel as the reaction. This invention is especially useful if the methanol is co-injected with hydrocarbons, or if the hydrocarbons formed in MTO are recycled in the oxygenate conversion zone.

This invention is especially useful if the zeolitic catalyst is selected from the MFI, MEL, clinoptilolite, FER, MWW, ZSM-22, ZSM-23, ZSM-42, ZSM-57 or a mixture thereof and is used in oxygenates conversion reactor. In this case one-pass selectivity to propylene is quite low so that olefins other than propylene have to be recycled to reactor inlet. This situation is different from MeAPO providing high one-trough light olefins yield. In addition MeAPO possess only a limited capability in recycling of heavy olefins.

On the other hand, these zeolitic catalysts are more stable on stream than MeAPO—like MTO catalyst. Therefore they can be used often in the process where the regeneration is performed in the same vessel. This allows to reduce the investment costs because of the absence of a separate regenerator vessel. The example of this process could be a process including moving beds, fixed beds or non-circulating fluidized bed reactors.

BACKGROUND OF THE INVENTION

US20040152935 discloses a method and system for reducing the formation of metal catalyzed side-reaction byproducts formed in the feed vaporization and introduction system of a methanol to olefin reactor system by forming and/or coating one or more of the heating devices, feed lines or feed introduction nozzles of/with a material that is resistant to the formation of metal catalyzed side reaction byproducts. The invention also may include monitoring and/or maintaining the temperature of at least a portion of the feed vaporization and introduction system and/or of the feedstock contained therein below about 400° C., 350° C., 300° C., 250° C., 200° C. or below about 150° C. The temperature can be maintained in the desired range by jacketing at least a portion of the feed vaporization and introduction system, such as at least a portion of the feed introduction nozzle, with a thermally insulating material or by implementing a cooling system. Said material that is resistant to the formation of metal catalyzed side reaction byproducts is preferably stainless steel such as AlSI (American Iron and Steel Institute) 316.

WO2007102916 relates to a process for producing light olefins from oxygenates wherein internal reactor surfaces are protected from metal-catalyzed coking preferably by employing a protective layer. A specific embodiment of this prior art is a process to convert a feed stream comprising an oxygenate in the reaction zone of a fast-fluidized-bed reactor at conversion conditions in the presence of a catalyst to yield a product stream comprising light olefins, wherein the one or more of the internal surfaces of the reaction zone comprises a protective layer resistant to metal-catalyzed coking. In this prior art is explained that metal-catalyzed coking leads to the formation of filamentous carbon, which promotes corrosion of reactor walls and coking of the catalyst. The carbon fibres may effect obstruction or clogging of moving parts (e.g., valve hinges) and increased pressure drops or even plugging of restricted spaces (e.g., diplegs). Metal-catalyzed coking also may be associated with carburization, although examination of iron surfaces exposed to conditions related to the present invention indicates that filamentous carbon is the principal concern. The protective layer may be formed on the one or more of the internal surfaces of the reaction zone. Effective materials can be selected from one or more of, tin, chromium, antimony, aluminum, germanium, bismuth, arsenic, gallium, indium, lead, copper, molybdenum, tungsten, titanium, niobium, zirconium, tantalum, hafnium, silver, gold, platinum, and mixtures, intermetallic compounds and alloys, as well as silicon and alumina. Preferred metals are selected from one or more of the group consisting of tin, chromium, nickel, antimony, aluminum, germanium and silicon. The metal-containing coatings can be applied by painting, electroplating, cladding, spraying, chemical vapor deposition, and sputtering. Preferably, the paint is a decomposable, reactive, metal-containing paint which produces a reactive metal which interacts with the reaction-zone internal surface. In a further alternative embodiment, one or both of aluminum and silicon can be applied to metal surfaces such as steels by well known deposition techniques.

A diluent can be mixed with methanol, said diluent is preferably steam.

It has now been discovered in the process of the previous prior art that not only coking is reduced but the undesired by-products such as CO, $CO_2$, methane and hydrogen are reduced and that such reduction of undesired by products is amplified by the presence of an hydrocarbon fed with the methanol.

It has been observed, in addition of the MTO reaction to produce olefins, a reforming of the methanol catalyzed by the inner surface of the reactor. Said reforming is significantly increased when ethylene or other hydrocarbon is co-fed with methanol in the MTO reactor over zeolite or phosphated zeolite.

It seems that this reforming of methanol is increased when the catalyst has been regenerated in the reactor. Without being binded by an explanation the inventors think that during the regeneration which is e.g. a burning of the coke present on the catalyst by air or air enriched with oxygen the temperature in the reactor can reach 500 to 800° C. and then the inner surface of the reactor gets catalytic properties.

It was found that the injection of a small amount of DMDS could significantly reduce this effect due to sulfidazing the reactor walls. This reduction is amplified when ethylene or other hydrocarbons is co-fed with methanol in the MTO reactor.

BRIEF DESCRIPTION OF THE INVENTION

The present invention is a process for making an olefin product from an oxygen-containing organic feedstock comprising:

providing a mixture of said oxygen-containing feedstock, an hydrocarbon and optionally an inert diluent, contacting said mixture in a reaction zone having an inner surface (the MTO reactor) with a zeolitic catalyst at conditions effective to convert at least a part of the oxygen-containing organic feedstock to olefin products (the MTO reactor effluent), recovering a reactor effluent comprising light olefins, a heavy hydrocarbon fraction and undesired by-products, wherein:

at least a part of the inner surface is passivated such that the undesired by-products are reduced by comparison with a non passivated inner surface and for one or more sulphur compound is co-injected with the said oxygen-containing feedstock and the hydrocarbon and said sulphur compound is capable to reduce the undesired by-products by comparison with a non injection of sulphur compound.

In a specific embodiment the catalyst is regenerated in the MTO reactor. Said regeneration is e.g. a treatment with air at a temperature around 500 to 800° C. to essentially burn the coke on the catalyst.

With regards to said effluent of the MTO reactor, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$.

According to a specific embodiment the MTO reactor effluent comprising light olefins and a heavy hydrocarbon fraction is sent to a fractionation section to separate said light olefins from said heavy hydrocarbon fraction; said heavy hydrocarbon fraction is recycled in the MTO reactor and is used as the hydrocarbon in the mixture of said oxygen-containing feedstock and hydrocarbon.

According to another embodiment of the invention said olefin products (the effluent of the MTO) are fractionated to form a stream comprising essentially ethylene and said stream in whole or in part is recycled in the MTO reactor inlet and is used as the hydrocarbon in the mixture of said oxygen-containing feedstock and hydrocarbon. In addition this increases the propylene yield of the MTO reactor.

According to another embodiment which is a combination of the two above embodiments, a stream comprising essentially ethylene and the heavy hydrocarbon fraction are recycled at the inlet of the MTO reactor and are used as the hydrocarbon in the mixture of said oxygen-containing feedstock and hydrocarbon.

In the above embodiments the MTO reactor can be a plurality of MTO reactors connected in series. This arrangement is advantageous when the MTO reactor is a fixed bed. To remove the heat of reaction the effluent of one of the reactors is cooled and optionally mixed with a fresh oxygen-containing feedstock before introduction in the subsequent MTO reactor.

The present invention is of high interest for the catalyst of the ZSM type such as ZSM-5 optionally containing phosphorus and regenerated in the MTO reactor.

In a specific embodiment the MTO reactor is fluidized bed reactor.

In a specific embodiment the MTO reactor is a non circulated fluidized bed reactor.

In a specific embodiment the catalyst is of the MFI type such as ZSM-5 optionally containing phosphorus.

In a specific embodiment the catalyst is regenerated in the MTO reactor (the oxygenates conversion reactor).

In a specific embodiment the catalyst is of the MFI type with Si/Al ratio at least 60 and used in fixed bed MTO process.

In a specific embodiment the catalyst is selected from MEL, FER, MTT, MWW, TON, EUO, MFS, ZSM-48.

DETAILED DESCRIPTION OF THE INVENTION

Metal-catalyzed coking leads to the formation of filamentous carbon, which promotes corrosion of reactor walls and coking of the catalyst. The carbon fibers may effect obstruction or clogging of moving parts (e.g., valve hinges) and increased pressure drops or even plugging of restricted spaces (e.g., diplegs). In the same time reactor walls can catalyse reforming of methanol or olefins co-feeded with methanol leading to hydrogen and methane formation.

As regards the passivation of the inner surface of the MTO reactor, the passivation means a treatment of at least a part of the inner surface such that the undesired by-products in the reactor effluent are reduced by comparison with a non passivated inner surface. Good results are achieved when one or more of the internal surfaces of the reaction zone of the present invention comprises a protective layer resistant to metal-catalyzed coking and metal dusting. Carburized internal surface as well as small metal particles transformed under reaction conditions to a corresponding carbide become an active catalyst for reforming process leading to undesired by-product such as CO, $CO_2$, $H_2$, $CH_4$ etc. This side reaction decreases significantly the ultimate carbon efficiency of oxygenates (e.g. MeOH) and hydrocarbon co-conversion to light olefins. The protective layer maintains the metals located in the inner surface in inactive form under reaction conditions. Non-limiting examples of inactive form of metals could be oxides, sulphur-containing compounds, nitrogen-containing compounds, phosphorous containing compounds etc. The protective layer may be formed on the one or more of the internal surfaces of the reaction zone using at least one of a variety of materials applied in any manner which is effective to provide a stable layer at conversion conditions. Effective materials can be selected from one or more of, without so limiting the invention, tin, chromium, antimony, aluminum, germanium, bismuth, arsenic, gallium, indium, lead, copper, molybdenum, tungsten, titanium, niobium, zirconium, tantalum, hafnium, silver, gold, platinum, and mixtures, intermetallic compounds and alloys, as well as silicon and alumina.

Preferred metals are selected from one or more of the group consisting of tin, antimony, aluminum, germanium and silicon.

The protective layer may be applied in any suitable manner which provides a stable layer at conversion conditions. For example, without so limiting the invention, metal-containing coatings can be applied by painting, electroplating, cladding, spraying, chemical vapor deposition, and sputtering. Painting is a preferred method of applying the protective layer. Such paint can be applied on reactor-system surfaces by any effective manner such as spraying, brushing, or pigging, Preferably, the paint is a decomposable, reactive, metal-containing paint which produces a reactive metal which interacts with the reaction-zone internal surface. Tin is a preferred metal and is exemplified herein; disclosures herein about tin are generally applicable to other reducible metals such as germanium. Preferred paints comprise a metal component selected from one or more of the group comprising: a hydrogen-decomposable metal compound, such as an organometallic compound; finely divided metal; a metal oxide, preferably a reducible metal oxide; and a solvent. A particularly preferred organometallic compound comprises one or more of butyl tin, tin octanoate or tin neodecanoate. It is within the scope of the invention that iron is added to a tin-containing paint to facilitate the reaction of the paint to form iron stannides as a flux.

In a further alternative embodiment, one or both of aluminum and silicon can be applied to metal surfaces such as steels by well known deposition techniques. Alternative processes include powder and vapor diffusion processes such as the "Alonizing" process, which has been commercialized by Alon Processing, Inc., Tarentum, Pa. Essentially, "Alonizing" is a high temperature diffusion process which alloys aluminum into the surface of a treated metal, such as steel, producing aluminides. Silicon can be applied by any effective method; for example, by diffusion coating as disclosed in U.S. Pat. No. 4,714,632; U.S. Pat. No. 5,254,369; and U.S. Pat. No. 5,873,951, the content of which is enclosed in the present invention. As disclosed in these patents, other materials such as aluminum and chromium may be combined with silicon in a protective coating. It is preferred that the coatings be sufficiently thick that they completely cover the base metallurgy and that the resulting protective layers remain intact over years of operation.

This thickness depends, inter alia, on the nature and effectiveness of the coating metal. In general, the thickness after curing is preferably between 0.1 and 50 mils, more preferably between 0.5 and 10 mils.

Although not necessary for all coating materials, for some coatings it is preferred that the coating be cured prior to use. This is especially true for coating materials containing reducible metal oxides and organometallic components, such as oxygen-containing organometallic compounds.

In a preferred embodiment, cure conditions comprise a heating step and optionally a reducing step in a hydrogen-containing atmosphere at elevated temperatures. Hydrogen contacting preferably occurs while the protective layer is being formed. In general, the contacting of the reactor system having a metal-containing coating, plating, cladding, paint or other coating applied to a portion thereof with a hydrogen-containing gas is done for a time and at a temperature sufficient to produce a continuous and uninterrupted protective layer which adheres to the substrate. Curing is preferably done over a period of hours, often with temperatures increasing over time. For example, tin paints are preferably cured between 420° and 600° C.

Alternatively or in addition to directly coating the one or more of the internal surfaces, a protective layer to reduce metal-catalyzed coking can be provided by introducing protective materials in the feed stream. Preferably the protective material is introduced as an organometallic compound which optimally is a hydrogen-decomposable compound.

Preferable organometallic compounds are selected from compounds of tin, chromium, antimony, aluminum and germanium, with tin compounds being especially favored. Such materials should be mobile and able to bond with the one or more of the internal surfaces. For example, one or more of butyl tin, tin octanoate and tin neodecanoate could be introduced into the feed stream in a concentration of from 0.01 to 500 wt-ppm. The organometallic compound may be introduced either on a continuous basis or on an intermittent basis in a cycle sufficient to provide a protective layer as described hereinbefore to reduce metal-catalyzed coking.

Suitable reaction conditions for the conversion of aliphatic hetero compounds vary by the nature of the feed stream and product objective. In general, reaction severity increases with increasing temperature, increasing catalyst activity, and decreasing space velocity.

Suitable conditions for the conversion of oxygenates to light olefins in accordance with the present invention comprise a temperature of from 200° to 600° C., preferably from 300° to 500° C., and a pressure of from 7 to 1400 kPa, preferably from 140 to 700 kPa.

As regards the injection of sulphur compound, one or more sulphur compound is co-injected with the said oxygen-containing feedstock and the hydrocarbon such that the undesired by-products in the reactor effluent are reduced by comparison with a non injection of sulphur compound. Sulphur compound means also a precursor of a sulphur compound. The man skilled in the art can easily determine, by following the by-products in the reactor effluent and the percentage of said by-products wether a sulphur compound is appropriate. Significant improvement can be achieved in case of injection of advantageously at least 10 vppm of sulfur compounds. Various sulphur compounds, advantageously sulfur degradable compounds such as thiols and sulfides of which dimethyldisulphide (DMDS) can be used. Amounts (in sulfur element) can range from 10 vppm to 1000 vppm and preferably from 50 vppm to 800 vppm, more preferably around 100 vppm.

One can cite sulphur compound in which sulphur is part of an aromatic heterocycle. The thiohydrocarbons can be selected from the group consisting of thiophene, benzothiophene, substituted thiophenes and mixtures thereof.

As regards the MTO process, the oxygenate feedstock is any feedstock containing a molecule or any chemical having at least an oxygen atom and capable, in the presence of the above catalyst, to be converted to olefin products. The oxygenate feedstock comprises at least one organic compound which contains at least one oxygen atom, such as aliphatic alcohols, ethers, carbonyl compounds (aldehydes, ketones, carboxylic acids, carbonates, esters and the like). Representative oxygenates include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Representative oxygenates include lower straight chain or branched aliphatic alcohols, their unsaturated counterparts. a preferred oxygenate is methanol or dimethyl ether or mixture thereof.

As regards the hydrocarbon, the ratio of oxygenate to hydrocarbon can be from 30/1 to 1/30, or from 10/1 to 1/10, or from 10/1 to 1/5.

As regards the catalyst, The present invention is not limited to specific catalysts.

In a preferred embodiment, a crystalline silicate containing advantageously at least one 10 members ring into the structure is used. The non-limited examples of zeolitic catalyst can be the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), MFS (ZSM-57) and ZSM-48 family of microporous materials consisting of silicon, aluminium, boron and oxygen.

Advantageously in said embodiment the catalyst is a crystalline silicate with MFI structure having a framework ratio Si/Al of at least about 60. Such crystalline silicate having a framework ratio Si/Al of at least about 60 and the dealuminated crystalline silicate are essentially in H-form. It means that a minor part (less than about 50%) can carry metallic compensating ions such as Na, Mg, Ca, La, Ni, Ce, Zn, Co.

Examples of a crystalline silicate of the MFI type are the synthetic zeolite ZSM-5 and silicalite and other MFI type crystalline silicates known in the art. Examples of a crystalline silicate of the MEL family are the zeolite ZSM-11 and other MEL type crystalline silicates known in the art. Other examples are Boralite D and silicalite-2 as described by the International Zeolite Association (Atlas of zeolite structure types, 1987, Butterworths).

In a specific embodiment the crystalline silicate is dealuminated by steaming to remove aluminium from the crystalline silicate framework. The steam treatment is conducted at elevated temperature, preferably in the range of from 425 to 870° C., more preferably in the range of from 540 to 815° C. and at atmospheric pressure and at a water partial pressure of from 13 to 200 kPa. Preferably, the steam treatment is conducted in an atmosphere comprising from 5 to 100% steam. The steam atmosphere preferably contains from 5 to 100 vol % steam with from 0 to 95 vol % of an inert gas, preferably nitrogen. A more preferred atmosphere comprises 72 vol % steam and 28 vol % nitrogen Le 72 kPa steam at a pressure of one atmosphere. The steam treatment is preferably carried out for a period of from 1 to 200 hours, more preferably from 20 hours to 100 hours. As stated above, the steam treatment tends to reduce the amount of tetrahedral aluminium in the crystalline silicate framework, by forming alumina.

In a more specific embodiment the crystalline silicate catalyst is dealuminated by heating the catalyst in steam to remove aluminium from the crystalline silicate framework and extracting aluminium from the catalyst by contacting the catalyst with a complexing agent for aluminium to remove from pores of the framework alumina deposited therein during the steaming step thereby to increase the silicon/aluminium atomic ratio of the catalyst. The catalyst having a high silicon/aluminium atomic ratio for use in the catalytic process of the present invention is manufactured by removing aluminium from a commercially available crystalline silicate. By way of example a typical commercially available silicalite has a silicon/aluminium atomic ratio of around 120. In accordance with the present invention, the commercially available crystalline silicate is modified by a steaming process which reduces the tetrahedral aluminium in the crystalline silicate framework and converts the aluminium atoms into octahedral aluminium in the form of amorphous alumina. Although in the steaming step aluminium atoms are chemically removed from the crystalline silicate framework structure to form alumina particles, those particles cause partial obstruction of the pores or channels in the framework. This could inhibit the process of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminium complex yields the overall effect of de-alumination of the crystalline silicate. In this way by removing aluminium from the crystalline silicate framework and then removing alumina formed there from the pores, the process aims at achieving a substantially homogeneous de-alumination throughout the whole pore surfaces of the catalyst. This reduces the acidity of the catalyst. The reduction of acidity ideally occurs substantially homogeneously throughout the pores defined in the crystalline silicate framework. Following the steam treatment, the extraction process is performed in order to de-aluminate the catalyst by leaching. The aluminium is preferably extracted from the crystalline silicate by a complexing agent which tends to form a soluble complex with alumina. The complexing agent is preferably in an aqueous solution thereof. The complexing agent may comprise an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The complexing agent may comprise an inorganic acid such as nitric acid, halogenic acids, sulphuric acid, phosphoric acid or salts of such acids or a mixture of such acids. The complexing agent may also comprise a mixture of such organic and inorganic acids or their corresponding salts. The complexing agent for aluminium preferably forms a water-soluble complex with aluminium, and in particular removes alumina which is formed during the steam treatment step from the crystalline silicate. A particularly preferred complexing agent may comprise an amine, preferably ethylene diamine tetraacetic acid (EDTA) or a salt thereof, in particular the sodium salt thereof. In a preferred embodiment, the framework silicon/aluminium ratio is increased by this process to a value about in the range 150 to 1000, more preferably at least 200.

Following the aluminium leaching step, the crystalline silicate may be subsequently washed, for example with distilled water, and then dried, preferably at an elevated temperature, for example around 110° C.

Additionally, if the ultimate alkaline metals content is high in the catalysts of the invention, the molecular sieve might be subjected to an ion-exchange step. Conventionally, ion-exchange is done in aqueous solutions using ammonium salts or inorganic acids.

Optionally the dealuminated zeolite may be further modified by metals or metals-containing compounds. The metal-containing compound may include metals chosen from one or more of Ca, Sr, Ba, La, Ce, Mg, Ga, Al, In, Cs, Sc, Sn, Li, Zn, Ag, Co, Mo, Mn, Ni, Fe, Cu, Cr, Ti and V. The metal-containing compounds may also additionally comprise phosphorus, sulphur, boron, silicon, nitrogen or being presented in form of oxide or hydroxide on the catalyst.

Following the de-alumination step, the catalyst is thereafter calcined, for example at a temperature of from 400 to 800° C. at atmospheric pressure for a period of from 1 to 10 hours.

According to another advantageous embodiment the catalyst is a P-modified zeolite (Phosphorus-modified zeolite).

Said phosphorus modified molecular sieves can be prepared based on MFI, MOR, MEL, clinoptilolite or FER crystalline aluminosilicate molecular sieves having an initial Si/Al ratio advantageously between 4 and 500. The P-modified zeolites of this recipe can be obtained based on cheap crystalline silicates with low Si/Al ratio (below 30).

By way of example said P-modified zeolite is made by a process comprising in that order:
selecting a zeolite (advantageously with Si/Al ratio between 4 and 500) among $H^+$ or $NH_4^+$-form of MFI, MEL, FER, MOR, clinoptilolite;
introducing P at conditions effective to introduce advantageously at least 0.05 wt % of P;
separation of the solid from the liquid if any;
an optional washing step or an optional drying step or an optional drying step followed by a washing step;
a calcination step; the catalyst of the XTO and the catalyst of the OCP being the same or different The zeolite with low Si/Al ratio has been made previously with or without direct addition of an organic template.

Optionally the process to make said P-modified zeolite comprises the steps of steaming and leaching. The method consists in steaming followed by leaching. It is generally known by the persons in the art that steam treatment of zeolites, results in aluminium that leaves the zeolite framework and resides as aluminiumoxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

P can be introduced by any means or, by way of example, according to the recipe described in U.S. Pat. No. 3,911,041, U.S. Pat. No. 5,573,990 and U.S. Pat. No. 6,797,851.

Optionally the P-modified zeolite comprises metals-containing compounds.

The metal-containing compound may include metals chosen from one or more of Ca, Sr, Ba, La, Ce, Mg, Ga, Al, In, Cs, Sc, Sn, Li, Zn, Ag, Co, Mo, Mn, Ni, Fe, Cu, Cr, Ti and V. The metal-containing compounds may also additionally comprise phosphorus, sulphur, boron, silicon, nitrogen or being presented in form of oxide or hydroxide on the catalyst.

The catalyst made of a P-modified zeolite can be the P-modified zeolite itself or it can be the P-modified zeolite formulated into a catalyst by combining with other materials that provide additional hardness or catalytic activity to the finished catalyst product.

The preferred catalyst may be, and preferably is, incorporated into solid particles in which the catalyst is present in an amount effective to promote the desired hydrocarbon conversion. In one aspect, the solid particles comprise a catalytically effective amount of the catalyst and at least one matrix material, preferably selected from the group consisting of binder materials, filler materials, and mixtures thereof to provide a desired property or properties, e.g., desired catalyst dilution, mechanical strength and the like, to the solid particles. Such matrix materials are often to some extent porous in nature and may or may not be effective to promote the desired hydrocarbon conversion. The matrix materials may promote conversion of the feed stream and often provide reduced selectivity to the desired product or products relative to the catalyst. Filler and binder materials include, for example, synthetic and naturally occurring substances such as metal oxides, clays, silicas, aluminas, silica-aluminas, silica-magnesias, silica-zirconias, silica-thorias, silica-beryllias, silica-titanias, silica-alumina-thorias, silica-alumina-zirconias, alumino-phosphates, mixtures of these, and the like.

If matrix materials, e.g., binder and/or filler materials, are included in the catalyst composition, the non-zeolitic and/or zeolitic molecular sieves preferably comprise 1 to 99 percent, more preferably 5 to 90 percent, and still more preferably 10 to 80 percent by weight of the total composition. The preparation of solid particles comprising catalyst and matrix materials is conventional and well known in the art and, therefore, need not be discussed in detail herein.

The foregoing disclosure and following examples are presented only to illustrate certain specific embodiments of the invention, and should not be construed to limit the scope of the invention as set forth in the claims. There are many possible other variations within the spirit of the invention, as those of ordinary skill in the art will recognize.

EXAMPLES

In the examples an MTO reaction was carried out at 550° C., P=1.5 bara, WHSV=1.6 $h^{-1}$ over an extruded with silica binder Ca—P-MFI catalyst containing 40 wt % of zeolite.

FIG. 1 (comparative I) illustrates by product concentrations ($H_2$, CO, CH4 and $CO_2$) in an MTO reaction effluent with pure methanol on fresh catalyst.

FIG. 2. (comparative II) illustrates by product concentrations ($H_2$, CO, CH4 and $CO_2$) in an MTO reaction effluent with a mixture of methanol and ethylene on fresh catalyst (methanol/ethylene 5/1 on C-basis).

Comparison the data presented at the FIGS. 1 & 2 clearly illustrates significant increase of the by-product formation in case of co-feeding of ethylene with methanol.

FIG. 3 (comparative III) illustrates by product concentrations ($H_2$, CO, CH4 and $CO_2$) in an MTO reaction effluent, further to a regeneration of the catalyst, fed with pure methanol and ethylene (methanol/ethylene 5/1 on C-basis, dry basis).

FIG. 4. (examples according to the invention) illustrates by product concentrations ($H_2$, CO, CH4 and $CO_2$) in an MTO reaction effluent, further to a regeneration of the catalyst, fed with methanol and DMDS (100 vppm of S). Then after 250 minutes ethylene is introduced, the by-products are lowered as compared with FIG. 2, 3 and even to the FIG. 1.

The invention claimed is:

1. A process for making an olefin product from an oxygen-containing organic feedstock comprising:
   contacting an oxygen-containing organic feedstock, ethylene, and a sulphur compound in a reactor comprising a passivated inner surface with a zeolitic catalyst at conditions effective to convert at least a part of the oxygen-containing organic feedstock to olefin products,
   wherein the sulphur compound is present in an amount ranging from 10 vppm to 1000 vppm, and wherein the sulphur compound comprises a thiol, dimethyldisulphide, or an aromatic heterocycle, wherein the ethylene and is present in the reactor at a ratio of oxygen-containing organic feedstock to ethylene ranging from 10:1 to 1:10.

2. The process according to claim 1 wherein a portion of the olefin products is sent to a fractionation section to separate light olefins from a heavy hydrocarbon fraction; wherein a portion of said heavy hydrocarbon fraction is recycled in the reactor as a portion of the hydrocarbon.

3. The process according to claim 1 wherein said olefin products are fractionated to form a stream comprising essentially ethylene and said stream in whole or in part is recycled in the reactor as a portion of the hydrocarbon.

4. The process according to claim 1 wherein the reactor comprises a plurality of reactors connected in series.

5. The process according to claim 1 wherein the reactor is further defined as a non-circulated fluidized bed reactor.

6. The process according to claim 1 wherein the reactor is further defined as a fluidized bed reactor.

7. The process according to claim 1 wherein the zeolitic catalyst comprises an MFI type zeolitic catalyst.

8. The process according to claim 7 wherein the MFI type zeolitic catalyst is further defined as a ZSM-5 optionally containing phosphorus.

9. The process according to claim 1 wherein the zeolitic catalyst is regenerated in the reactor.

10. The process according to claim 1 wherein the zeolitic catalyst is of the MFI type zeolitic catalyst with Si/Al ratio at least 60.

11. The process according to claim 1 wherein the zeolitic catalyst is selected from a group consisting of MEL, MIT, MWW, TON, EUO, and MFS.

12. The process according to claim 1, wherein the sulphur compound is present in an amount ranging from 50 vppm to 800 vppm.

13. The process according to claim 1, wherein the sulphur compound comprises the thiol.

14. The process according to claim 1, wherein the sulphur compound comprises the aromatic heterocycle.

15. The process according to claim 1, wherein the sulphur compound is introduced into the reactor prior to the ethylene.

16. The process according to claim 14, wherein the aromatic heterocycle is selected from a group consisting of thiophene, benzothiophene, substituted thiophenes and combinations thereof.

17. The process according to claim 1, wherein the ethylene is a reactive co-feed and is present in the reactor at a ratio of oxygen-containing organic feedstock to ethylene ranging from 30:1 to 1:30.

18. The process of claim 1, wherein the ethylene is present in the reactor at a ratio of oxygen-containing organic feedstock to ethylene ranging from 10:1 to 1:5.

19. A process for making an olefin product from an oxygen-containing organic feedstock comprising:
 providing a mixture of the oxygen containing organic feedstock, ethylene, and optionally an inert diluent;
 contacting the mixture in a reaction zone having an inner surface with a zeolitic catalyst at conditions effective to convert at least a part of the oxygen-containing organic feedstock to olefin products;
 recovering a reactor effluent comprising light olefins, a heavy hydrocarbon fraction, and by-products;
 wherein:
 at least a part of the inner surface is passivated;
 one or more sulphur compounds are co-injected with the oxygen-containing organic feedstock and the ethylene;
 wherein the sulphur compound is present in an amount ranging from 10 vppm to 1000 vppm; and
 wherein the ethylene is present in the reactor at a ratio of oxygen-containing organic feedstock to ethylene ranging from 10:1 to 1:10.

\* \* \* \* \*